(12) United States Patent
Sarma et al.

(10) Patent No.: US 11,701,271 B2
(45) Date of Patent: *Jul. 18, 2023

(54) ANTENNA AND SYSTEM FOR WIRELESS SENSING OF HEALTH MONITORING

(71) Applicant: Massachusetts Institute of Technology, Cambridge, MA (US)

(72) Inventors: Sanjay E. Sarma, Lexington, MA (US); Rahul Bhattacharyya, Portland, ME (US); Joshua E. Siegel, Brookline, MA (US); Alex Armengol Urpi, Sant Sadurni d'Anoia (ES); Pankhuri Sen, Cambridge, MA (US); Sai Nithin Reddy Kantareddy, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/512,857

(22) Filed: Oct. 28, 2021

(65) Prior Publication Data

US 2022/0047431 A1 Feb. 17, 2022

Related U.S. Application Data

(63) Continuation of application No. 16/567,054, filed on Sep. 11, 2019, now Pat. No. 11,185,449.

(Continued)

(51) Int. Cl.
*G06K 7/08* (2006.01)
*A61F 13/42* (2006.01)
(Continued)

(52) U.S. Cl.
CPC .......... *A61F 13/42* (2013.01); *G06K 7/10297* (2013.01); *G06K 19/0717* (2013.01);
(Continued)

(58) Field of Classification Search
CPC ................ A61F 13/42; A61F 2013/424; A61F 2013/426; A61F 2013/427; G06K 19/027;
(Continued)

(56) References Cited

U.S. PATENT DOCUMENTS 6,165,386 A 12/2000 Endo et al.
7,176,344 B2 2/2007 Gustafson et al.
(Continued)

FOREIGN PATENT DOCUMENTS

CN 106767967 5/2017
CN 109636433 4/2019
(Continued)

OTHER PUBLICATIONS

Extended European Search Report for EP19859840.1 dated May 13, 2022.
(Continued)

*Primary Examiner* — Thien M Le
(74) *Attorney, Agent, or Firm* — Peter A. Nieves; Nieves IP Law Group, LLC (57) ABSTRACT

An agent activated non-metal antenna for an ultra-high frequency (UHF) wireless sensor having a radio frequency identification (RFID) tag in electronic communication with the non-metal antenna, and a wireless data communication integrated circuit (IC), includes a conductive stimuli-responsive hydrogel material configured to be inactive prior to an interaction with an activating agent and active upon the interaction with the activating agent. The antenna is further configured to transmit power to turn on the wireless data communication IC only when the non-metal antenna is active upon interaction with the activating agent.

15 Claims, 8 Drawing Sheets

Related U.S. Application Data (60) Provisional application No. 62/730,384, filed on Sep. 12, 2018.

(51) Int. Cl.
*G06K 7/10* (2006.01)
*G06K 19/07* (2006.01)

(52) U.S. Cl.
CPC ... *A61F 2013/424* (2013.01); *A61F 2013/426* (2013.01); *A61F 2013/427* (2013.01); *G06K 2007/10504* (2013.01)

(58) Field of Classification Search
CPC ......... G06K 19/0717; G06K 19/07773; G06K 2007/10504; G06K 7/10297
See application file for complete search history.

(56) References Cited

U.S. PATENT DOCUMENTS

| | | | |
|---|---|---|---|
| 7,342,550 B2 * | 3/2008 | Sanford | H01Q 13/18 343/771 |
| 8,985,448 B2 | 3/2015 | Jonely | |
| 2001/0018793 A1 | 9/2001 | McKinnon et al. | |
| 2004/0070510 A1 | 4/2004 | Zhang et al. | |
| 2004/0220538 A1 | 4/2004 | Panopoulos | |
| 2004/0095247 A1 | 5/2004 | De Haan et al. | |
| 2005/0033250 A1 | 2/2005 | Collette et al. | |
| 2006/0080819 A1 * | 4/2006 | McAllister | G06K 17/00 29/403.3 |
| 2006/0243043 A1 * | 11/2006 | Breed | B60C 23/041 73/146 |
| 2006/0244614 A1 | 11/2006 | Long | |
| 2007/0057781 A1 * | 3/2007 | Breed | B60K 35/00 340/457.1 |
| 2007/0083174 A1 | 4/2007 | Ales et al. | |
| 2007/0096565 A1 * | 5/2007 | Breed | B60C 23/0408 200/600 |
| 2007/0108296 A1 * | 5/2007 | Konopka | G06K 19/07771 235/487 |
| 2007/0271014 A1 * | 11/2007 | Breed | B60R 21/0152 701/31.9 |
| 2008/0114502 A1 * | 5/2008 | Breed | G02B 27/01 701/2 |
| 2008/0269702 A1 | 10/2008 | Ales et al. | |
| 2009/0036850 A1 | 2/2009 | Nhan et al. | |
| 2009/0155918 A1 | 6/2009 | Payen et al. | |
| 2009/0201142 A1 | 8/2009 | Zou et al. | |
| 2009/0326417 A1 | 12/2009 | Ales, III et al. | |
| 2010/0114046 A1 | 5/2010 | Ales et al. | |
| 2010/0168702 A1 | 7/2010 | Ales, III et al. | |
| 2010/0237038 A1 | 9/2010 | Chiang | |
| 2010/0241094 A1 | 9/2010 | Sherron | |
| 2012/0089299 A1 * | 4/2012 | Breed | G01S 15/88 701/1 |
| 2012/0092027 A1 | 4/2012 | Forster | |
| 2012/0119915 A1 | 5/2012 | Clement et al. | |
| 2012/0310190 A1 | 12/2012 | Lavon et al. | |
| 2013/0036803 A1 | 2/2013 | Itou et al. | |
| 2013/0041334 A1 | 2/2013 | Prioleau et al. | |
| 2013/0076509 A1 | 3/2013 | Ahn | |
| 2013/0110061 A1 | 5/2013 | Abraham et al. | |
| 2013/0110063 A1 | 5/2013 | Abraham et al. | |
| 2013/0140371 A1 * | 6/2013 | Omura | G06K 19/07771 235/492 |
| 2014/0203915 A1 | 7/2014 | Puleston et al. | |
| 2014/0327546 A1 | 11/2014 | Carney et al. | |
| 2014/0333442 A1 | 11/2014 | Carney | |
| 2014/0350503 A1 | 11/2014 | Bosaeus et al. | |
| 2016/0178553 A1 | 6/2016 | Bommarito | |
| 2016/0328584 A1 * | 11/2016 | Rokhsaz | G06K 7/10326 |
| 2017/0348162 A1 | 12/2017 | Arizti et al. | |
| 2018/0104114 A1 | 4/2018 | Pepin et al. | |

FOREIGN PATENT DOCUMENTS

| | | |
|---|---|---|
| JP | 2005000602 | 1/2005 |
| JP | 2015146870 | 8/2015 |
| WO | 2005119195 | 12/2005 |
| WO | 2008052811 | 5/2008 |
| WO | 2014018109 | 1/2014 |

OTHER PUBLICATIONS

International Search Report and Written Opinion for PCT/US19/50520, dated Dec. 4, 2019.
Vox; "The Smart diaper is coming. Who actually wants it?"; May 2, 2019; https://www.vox.com/the-goods/2019/5/2/18525487/smart-diaper-huggies-monit-pampers-alert-poop-pee.
CviLux Corporation, "Opro9 Smart Wearable Humidity Sensor Instant Alert Prevent Baby Diaper" https://www.amazon.com/Wearable-Humidity-Sensor-Instant-Prevent/dp/B01N8RD32C; Date First Available : Jan. 17, 2017.
CNET, "The Smart Diaper Has Entered the Building at CES 2019" Jan. 2019, https://www.cnet.com/news/the-smart-diaper-has-entered-the-building-at-ces-2019/.
Mole, Beth, "Alphabet's Verily has a smart diaper design that distinguishes pee from poo", https://arstechnica.com/science/2018/05/smart-diaper-by-alphabets-verily-would-skip-sniff-test-to-answer-1-or-2/, May 17, 2018.

* cited by examiner

ANTENNA AND SYSTEM FOR WIRELESS SENSING OF HEALTH MONITORING

CROSS-REFERENCE TO RELATED APPLICATIONS

This application is a continuation of co-pending U.S. patent application Ser. No. 16/567,054, filed Sep. 11, 2019, entitled "System and Method for Wireless Sensing of Health Monitoring," which claims the benefit of U.S. Provisional Patent Application Ser. No. 62/730,384, filed Sep. 12, 2018, entitled "System, Material and Methods to Improve the Performance of Wireless Sensing in Health Monitoring Applications," which are incorporated by reference herein in their entirety.

FIELD OF THE INVENTION

The present invention relates to wireless sensors, and more particularly, is related to hydrogel-based tag antenna-based sensors to improve wireless sensing for health monitoring.

BACKGROUND OF THE INVENTION

The diaper industry is growing globally with a compound annual growth rate of 4-6% until 2020 as predicted by market analysts in different studies. This is also happening in a rapidly changing market landscape where technology infusion is being adopted/included as a key differentiating factor between different products. Existing "smart-diaper" solutions in the marketplace externally fabricated sensors into the diapers, which have several disadvantages. For example, these sensors are expensive compared to the price point of disposable diapers, making them economically feasible to commercialize. As a result, companies are targeting non-disposable diapers. Further, these sensors require a battery for to communicate with an external reader. The form factor is large, making it difficult to embed within the layers of the modern diaper. Also, these solutions contain metal, and are therefore not perceived as safe and/or comfortable. Therefore, there is a need in the industry to address one or more of these shortcomings.

SUMMARY OF THE INVENTION

Embodiments of the present invention provide an antenna and system for wireless sensing of health monitoring. Briefly described, a first aspect of the present invention is directed to an agent activated non-metal antenna for an ultra-high frequency (UHF) wireless sensor having a radio frequency identification (RFID) tag in electronic communication with the non-metal antenna, and a wireless data communication integrated circuit (IC), includes a conductive stimuli-responsive hydrogel material configured to be inactive prior to an interaction with an activating agent and active upon the interaction with the activating agent. The antenna is further configured to transmit power to turn on the wireless data communication IC only when the non-metal antenna is active upon interaction with the activating agent.

A second aspect of the present invention is directed to a UHF wireless sensor having an agent activated non-metal antenna with a conductive stimuli-responsive hydrogel. The sensor includes an RFID tag in electronic communication with the non-metal antenna and a wireless data communication IC in communication with the non-metal antenna and the RFID tag. The wireless data communication IC receives power to turn on from the agent activated non-metal antenna.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principles of the invention.

DETAILED DESCRIPTION

The following definitions are useful for interpreting terms applied to features of the embodiments disclosed herein, and are meant only to define elements within the disclosure.

As used within this disclosure, a "reader" refers to a passive RFID reader.

As used within this disclosure, "RFID chip" or "RFID tag" generally refers to a passive radio frequency identification IC chip, where the chip is powered by the radio energy transmitted by the reader. This is in contrast with a semi-active or active tag which takes power from external source such as energy harvester or battery to turn on the chip to backscatter the incident RF signal. For a passive tag, a fraction of incident RF energy is harvested by the chip to power itself, so the chip does not require any form of external power source.

As used within this disclosure, "backscatter" (or "backscattering") refers to the reflection of a signal transmitted by a reader back to the reader.

As used within this disclosure, an "activating agent" refers to a fluid configured to interact with a hydrogel material such that the hydrogel material behaves as an antenna. Exemplary activating agents and hydrogel materials may be found in Table 1.

As used within this disclosure, an antenna and/or RFID tag is said to be "inactive" when the antenna does not convey sufficient energy to the RFID tag for the RFID tag to function in the presence of an interrogating signal from an RFID reader. An antenna and/or RFID tag is said to be "active" when the antenna has been exposed to and transformed by an activating agent so that the antenna conveys sufficient energy to the RFID tag for the RFID tag to function in the presence of an interrogating signal from an RFID reader.

As used within this disclosure, ultra-high frequency (UHF) refers to electromagnetic energy in the range, preferably, but not limited to between 902 MHz and 928 MHz (based on wireless standards at the time of filing), but also reasonably between 300 MHz to 3-5 GHz as new wireless standards emerge.

Reference will now be made in detail to embodiments of the present invention, examples of which are illustrated in the accompanying drawings. Wherever possible, the same reference numbers are used in the drawings and the description to refer to the same or like parts.

Embodiments of the present invention employ TABS (tag antenna based sensing) utilizing low cost RFID tags integrated with smart materials such as hydrogels and readers. RFID tags can leverage characteristics of the antenna (tag). For example, antennas can be sensitive to different factors such as physical attributes, chemicals, gases, etc., by designing an antenna in a particular fashion with/without using smart materials. Due to any state change (either change in physical properties or introduction of a gas/chemical), electromagnetic response of the tag changes. This change in response can be attributed to the cause, here, a change in the physical attribute or presence of chemical/gas. Sensing is based on the tag antenna alone instead of electronics is referred to as TABS.

The embodiments include hydrogel-based tag sensors for improved wireless sensing for use, for example, in health monitoring. Hydrogel materials show mechanical and electrical response towards moisture and pH of the reactant. Moreover, various research studies show hydrogels can be tuned to detect biochemicals such as, for example, glucose. Furthermore, hydrogel materials may be FDA approved making them suitable candidates for human health monitoring. Embodiments of the present invention illustrate a fully/partially-hydrogel-based sensor to detect moisture and pH of the reacting solution wirelessly. While the embodiments presented here are directed to detecting baby diaper wetness, the invention is not limited to this application.

As noted in the background section, existing "smart-diaper" solutions in the market are using external sensors put into completed diapers. In contrast, under the embodiments, sensors are seamlessly integrated between the layers of the diaper material during the manufacturing process. A first embodiment hydrogel-based sensor 100 (FIG. 1A) and a second embodiment hydrogel based sensor 150 (FIG. 1B) may be embedded into the diaper or other sanitary products. The sensors 100 (FIG. 1A), 150 (FIG. 1B) are battery-less and communicate with the other component of a system including an RFID reader 130, purely on backscattering, described further below. The embodiments may use, for example, an RFID reader 130 compliant with the RFID UHF Gen 2 protocol. Both the first embodiment 100 and second embodiment 150 include an RFID integrated circuit 120. The first embodiment may further employ additional manufacturing considerations, such as hydrophobic coating for some applications.

Figure 1A:
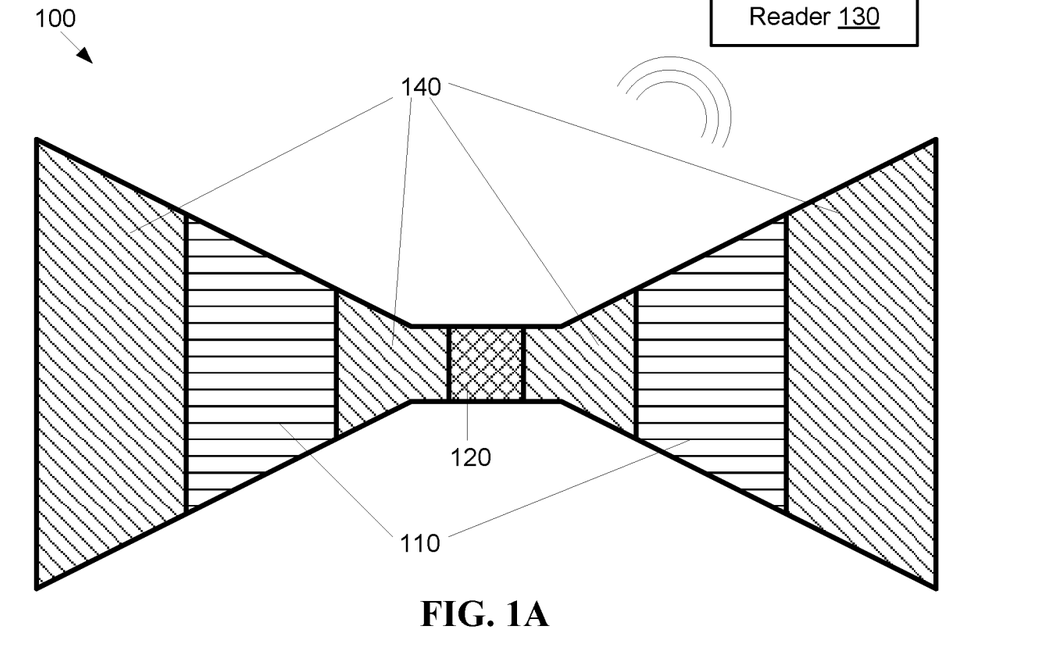
FIG. 1A is a schematic diagram showing a first embodiment of a moisture sensor.
Figure 1B:
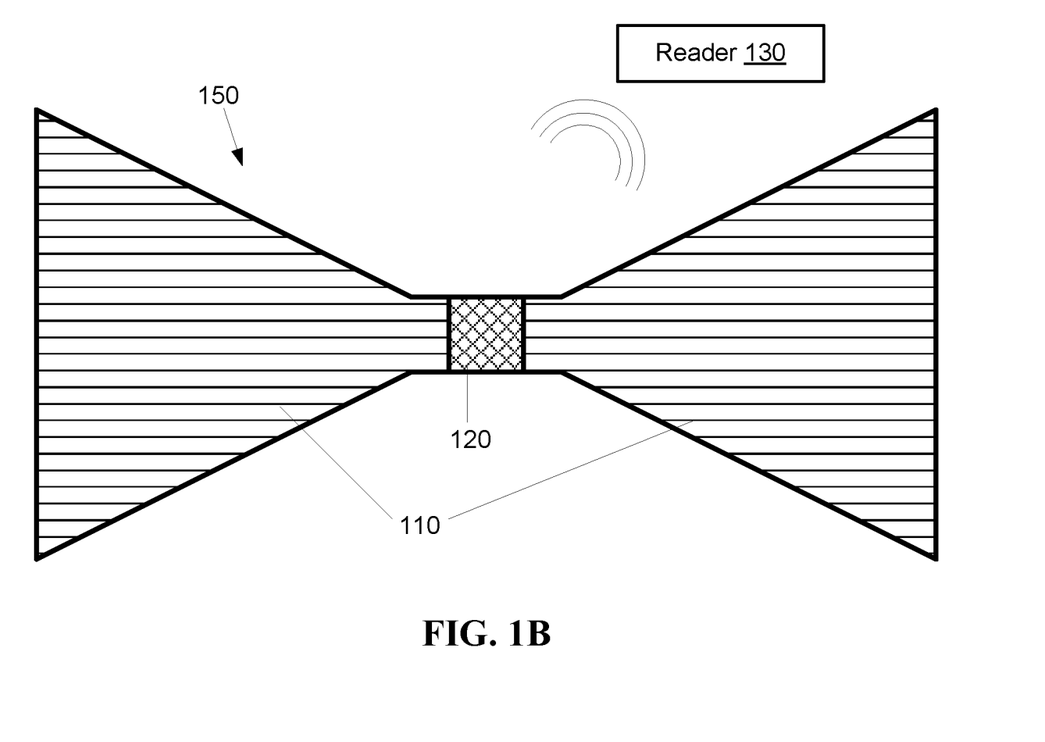
FIG. 1B is a schematic diagram showing a second embodiment of a moisture sensor.

As shown by FIG. 1B, a second embodiment sensor 150 is partially made of stimuli-responsive hydrogel material 110 and an RFID chip 120. The first embodiment sensor 100, shown by FIG. 1A, is partially made of stimuli-responsive hydrogel material 110, and partially made of an electrically conductive material 140 such as copper or silver, as shown in FIG. 1B. There is no chemical bonding between the hydrogel material 110 and the conductive material 140, just an overlapping region between the hydrogel material 110 and the conductive material 140. The fully hydrogel based sensor 150 of the second embodiment does not contain any extra metal 140 such as copper which otherwise may be a concern for products which are frequently in contact with human body.

Figure 2A:
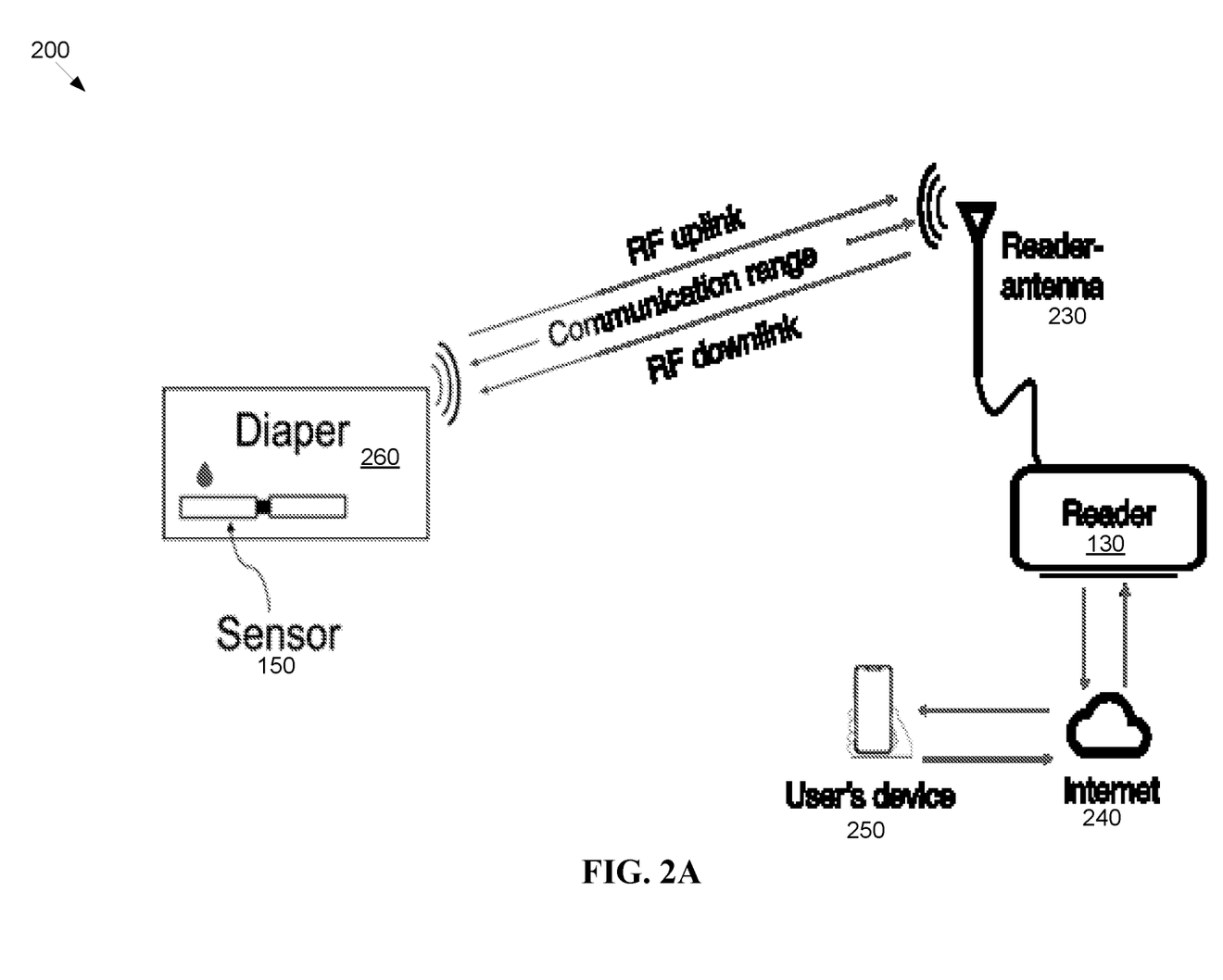
FIG. 2A is a first schematic diagram of a system for detecting moisture in a diaper.
Figure 2B:
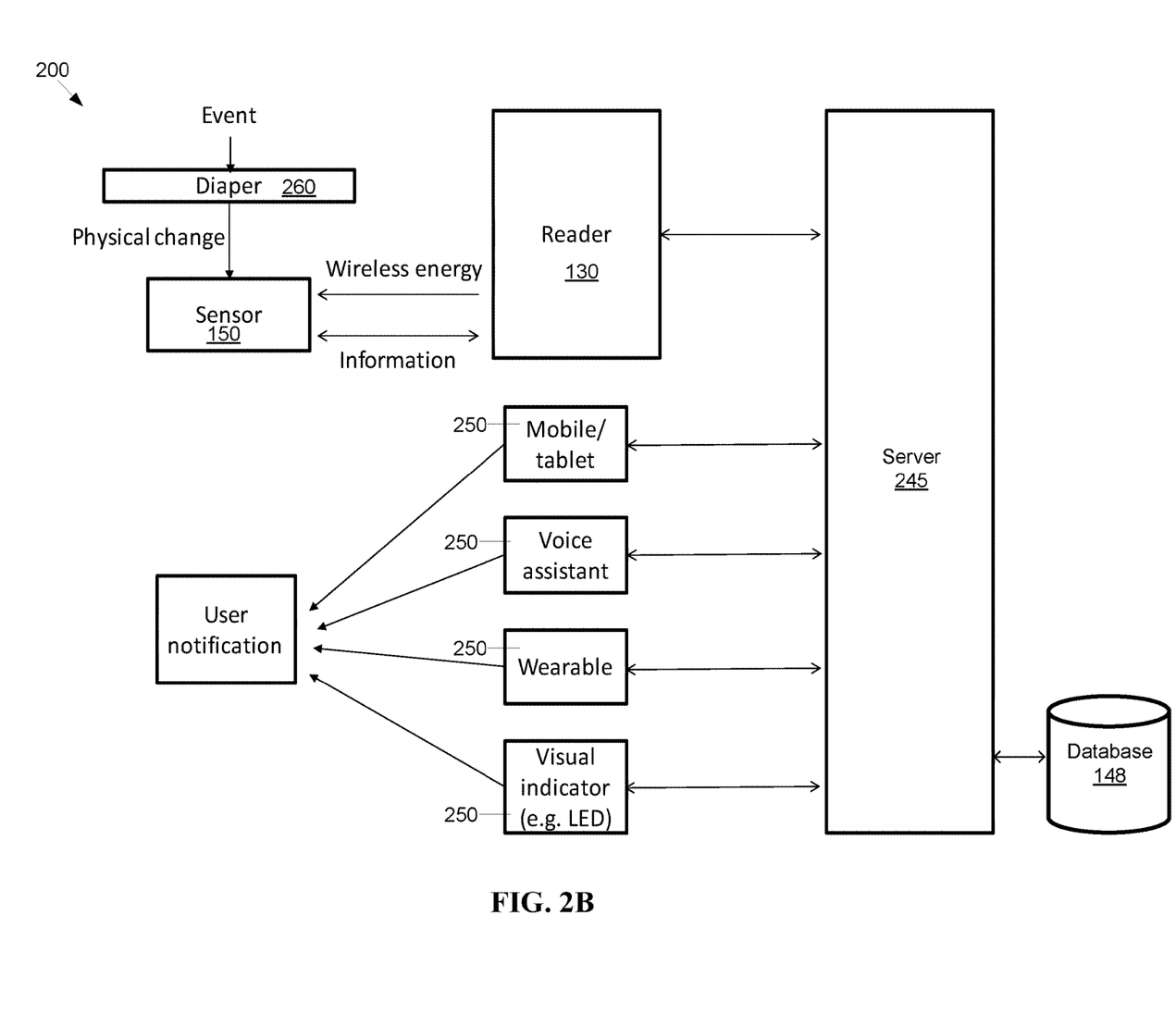
FIG. 2B is a second schematic diagram of a system for detecting moisture in a diaper.

FIGS. 2A and 2B show an exemplary system 200 for deploying the sensor 100, 150. While FIGS. 2A-2B show the second embodiment sensor 150, it is understood that either the first embodiment sensor 100 or the second embodiment sensor may be used in the system 200. For purposes of conciseness, the description generally refers only to the second embodiment sensor 150. The sensor 150 is deployed within a diaper 260. The reader 130 receives and transmits RF uplink/downlink signals via a reader antenna 230. The reader 130 may also communicate via a wired or wireless network, such as the internet 240, with a user device 250, for example a smart phone, tablet computer, or computer. Initially, the diaper is dry, so the sensor 150 is inactive.

Typically, all disposable diapers 260 contain a mixture of fluff and hydrogel. Fluff is sourced from cellulose based products. Hydrogel might vary from one diaper to another, but they generally fall into the broader category of Super Absorbent Polymers. For example, the diaper 260 may structurally include a top-sheet, a hydrophilic layer that enables rapid absorption of liquid to ensure the skin with which it is in contact stays dry. A distribution layer drains and disperses the moisture to the below layer's larger absorption volume. A third layer, the absorption layer, absorbs and retains the moisture inside the diaper. This layer is the thickest, consisting of Super Absorbent Polymer (SAP), a gel-like element contained within the fluff. Fluff, a non-woven material derived from cellulose, facilitates rapid absorption, whereas SAP provides the ability to retain moisture under pressure, reducing leakage. A bottom-sheet is the fourth layer, a hydrophobic layer for repelling moisture and keeping it from seeping through the diaper. Additional features such as fasteners, tapes, elastics, and leg cuffs augment this arrangement to ensure a good fit and prevent leakage.

While the type of diaper 260 material may affect the signal from the sensor 100, 150, most diapers should not dramatically, it is possible the diaper may alter the pH of the fluid depending on their absorption mechanism. However, this may be addressed in the design phase by reconfiguring the antenna geometry. While diaper material generally does not attenuate RF significantly, some attenuation is possible from gel-heavy diapers.

FIG. 2B is a more detailed drawing of an embodiment of a system for deploying the sensor 100, 150. Here, the reader 130 is in communication with a server 245, for example a cloud based server in communication with the reader via an internet connection. The server may be in communication with a database 148, for example, an internal or external database to store configuration parameters for the sensor 150 and/or state data regarding the sensor 150. FIG. 2B shows several possible end user interfaces 250, including a mobile computer/tablet, a voice assistant, a wearable, and a visual indicator (e.g., LED), which may be used to provide a user notification when the system detects a change in state of the diaper as indicated by the sensor 150.

Hydrogels 110 used in the sensor 150 not only physically respond to pH and moisture but also become good conductors as they change shape from an initial powdery state to semi-solid/solid state. For example, an activated hydrogel may have a conductivity of about $10^{-3}$ S/cm to 10 S/cm.

The first embodiment 100 and second embodiment 150 sensors exploit this phenomenon to behave as on/off sensors to detect moisture and pH, for example with a threshold greater than 5 ml, where changes in signal strength may be detected in steps of 10 ml. When the diaper 260 is dry, the conductivity of the hydrogel 110 is too low to function as an antenna. Therefore, the hydrogel 110 cannot transfer sufficient radio frequency (RF) power to the RFID chip 120 turn on the RFID chip 120. The source of power is the energy harvested by the IC 120 from the RF downlink signal. Initially, the reader 130 does not receive a backscattered signal indicating an "off scenario" because the diaper 260 is dry. When the diaper 260 is wet, the conductivity of the hydrogel 110 increases so the hydrogel 110 acts as an antenna. For example, if 0 dBm of power is received at the IC 120, −21 dBm of the power is used in powering up the IC 120 and 50-80% of the rest is backscattered to the reader. Therefore, the RFID chip 120 backscatters the RF signal which is detected by the reader 130. This indicates that the sensor 150 is in "on" mode because the diaper 260 is wet which increased the conductivity of the hydrogel material 110.

In the second embodiment 150, the sensor is constructed by patterning hydrogel powder into an RFID antenna shaped as a bow-tie. In alternative embodiments, other antenna shapes may be used, for example, dipole, squiggle, meander line, T-matched, etc.

Different hydrogel materials may be selected for specific applications. For example, under the second embodiment, a superabsorbent polymer (SAP) hydrogel material commonly found in the diapers was used to construct the antenna. This material is sensitive to water (pH=7) and lower pHs, down to pH=3. This falls in the range of pH of human urination, as is appropriate for a diaper application. Such a hydrogel material 110 does not respond to high pH solutions, but responds rather quickly to low pH solutions. However, other hydrogels may be tuned, for example via doping to detect different pH ranges. For example, a hydrogel may be tuned/doped by adding salt to change the aggregate's electrochemical properties. The second embodiment sensor 150 readily reacts with moisture/water and changes to semi-solid (partially rigid and fluidic) state starting to show electromagnetic properties of an RFID antenna. For example, hydrogels 110 may be selected for an application to react with specific bodily fluids, such as blood, pus, and/or sweat, as shown by table 1:

TABLE 1

| Fluid-Hydrogel pairings | | |
|---|---|---|
| Fluid | Hydrogel | Notes |
| Blood | polysaccharide κ-carrageenan (κCA), | loaded with synthetic two-dimensional (2D) nanosilicates |
| Sweat | pHEMA | *pH: Humic acid embedded chitosan/poly (vinyl alcohol) pH-sensitive hydrogel |
|  | Humic acid embedded |  |

TABLE 1-continued

| Fluid-Hydrogel pairings | | |
|---|---|---|
| Fluid | Hydrogel | Notes |
|  | chitosan/poly (vinyl alcohol) pH-sensitive hydrogel Via |  |
| Ammonia | poly ethylene glycol) diacrylates (PEG-DAs) 2-(dimethylamino)ethyl methacrylate (DMAEMA) Chitosan/Gelatin composite |  |

The semi-solid/solid hydrogel 110 antenna with the help of the Integrated Chip (IC) 120 already attached to the IC chip 120 functions like a traditional RFID tag. By monitoring this raw signal data, the reader 130 can infer a wetness event (when the moisture contacted the hydrogel 110). The signal strength received by the reader 130 is correlated to intensity of wetness in the diaper 230. The read intensity may be correlated to wetness within a cloud server 245 (FIG. 2B) or an end-use device 250 (FIG. 2B). In alternative embodiments, a second process/processor in the reader may be used to perform the correlation.

For example, the signal strength in dBm can be compared with the historical trend. An increasing RF uplink signal strength generally indicates the presence of more moisture. For example, a signal strength of −50 dBm may indicate a weak antenna possible due to the dry state. Once the diaper 260 becomes wet and sensor 150 becomes more conductive, the signal strength increases to −20 dBm. This increase in signal strength can be attributed to wetness in the diaper 260.

The sensor 100, 150 does not have an onboard battery and is completely passive. The sensor 100, 150 harvests power from the RF radiation reaching the sensor 150 through the diaper 260. Therefore, the duty cycle of the sensor 100, 150 is dependent on how fast the reader 130 collects samples. Typical rates can range from 100 Hz to 0.1 Hz. The reader 130 may be configured to interrogate the sensor 100, 150 in the diaper 260 continuously or at fixed frequencies as configured by the user. Examples of typical frequencies include once per minute, once per 5 minutes, once per 10 minutes, etc.

Signal frequency used for the sensor 100, 150 may be implemented according to mandated frequency RFID standards. For example, in the North American region and Argentina the frequency range is 902-928 MHz. In India: 865-867 MHz, China: 779-787 MHz, EU: 863-870 MHz and in Chile and Brazil: 915-928 MHz. Typical sensitivities for the chips (ICs) in terms of power range from −8 dBm to −31 dBm. The embodiments do not use resonant frequency sweeps to determine when the diaper is wet.

Figure 3:
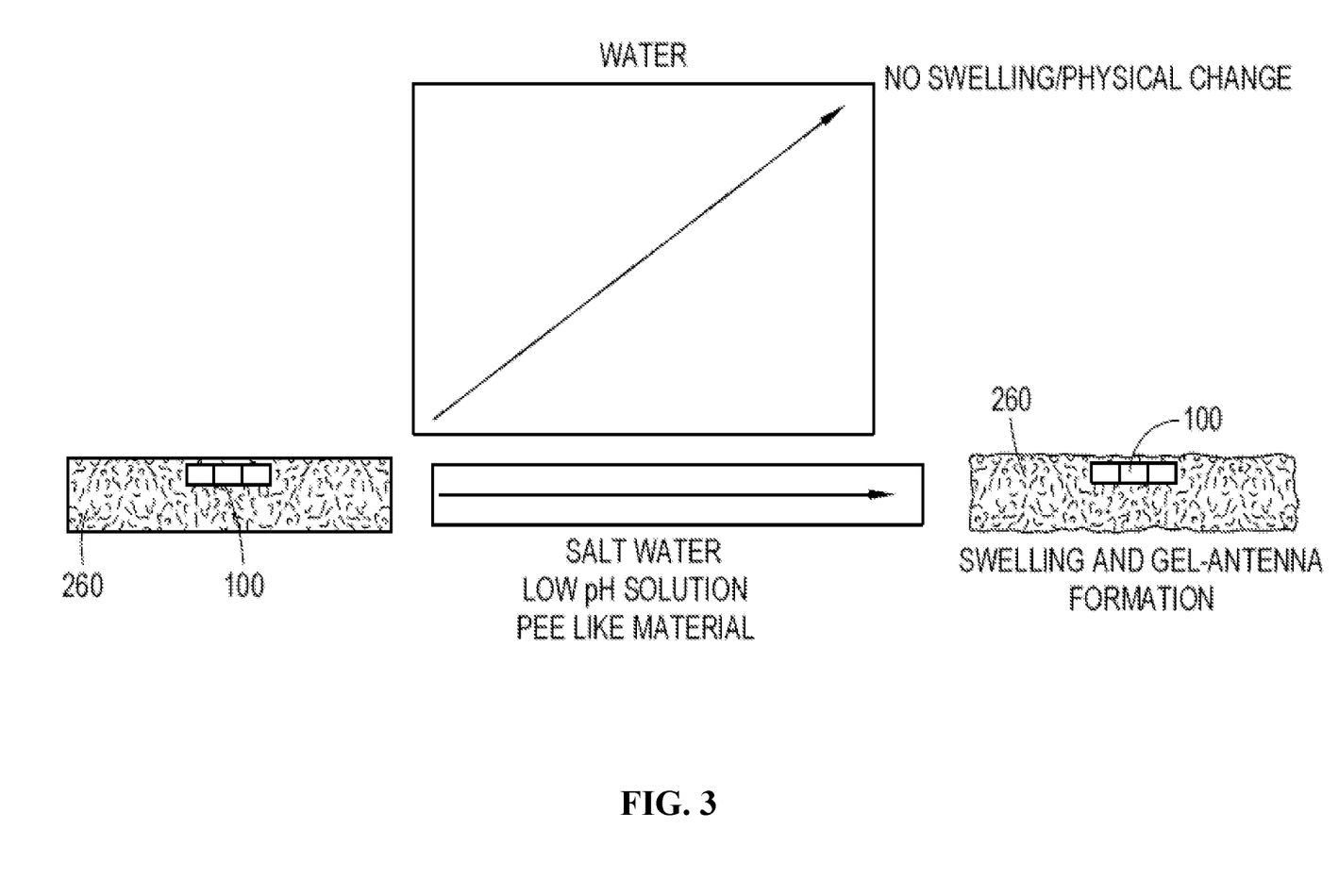
FIG. 3 is a diagram of the response of the first/second embodiment moisture sensor in the presence of alcohol and water.

FIG. 3. illustrates the sensing behavior where, in a first scenario (bottom) the hydrogel 110 in the diaper 260 swells and takes the shape of an antenna for the sensor 100 in the presence of water. In a second scenario (top) where the diaper is exposed to Iso Propyl Alcohol (IPA), the hydrogel in the sensor 100 does not react, so there is no swelling and/or physical change in the sensor 100, so the sensor 100 remains in the "off" state.

Different antenna shapes such as bow tie shape and meander shape may be arranged to suit the form factor of the product and read range requirements. While FIG. 3 shows a sensor 100 contain a trace of copper as contacts between the IC and the hydrogel material, however, that is not necessary if hydrogel can be appropriately patterned to form contacts with the IC 120. For example, the hydrogel 110 can be patterned in the shape of bow tie shaped antenna, where the central terminals of the antenna electrically connect to the terminals of the IC 120.

The exemplary embodiments use conductive epoxy at the edges of the IC 120 to establish an electrically conductive contact with the hydrogel 110. The hydrogel 110 is placed at the ends of conductive epoxy and expands when wet. Hydrogel powder is attached to the substrate of the IC 120 with adhesive. In some applications the hydrogel 110 may be patterned directly on to the diaper layers using an adhesive in the shape of an antenna. The IC 120 is then attached in the desired position making electrical connection with the hydrogel 110 using epoxy or conductive ink (silver, copper, etc.). The RFID IC 120 has ports for connection to antenna terminals. Electromagnetic waves from the reader 130 induce potential difference across these antenna terminals. The IC 120 contains a passive power converter that rectifies this induced AC voltage into a continuous DC voltage to power up the IC 120.

Returning to FIG. 1A, in the first embodiment the sensor 100 can be made of a metal 140 as well as hydrogel 110. Since metal is a good conductor, it acts as a good radiating element, so providing an antenna made of metal, for example copper and silver, may increase the backscattering range of the reader-antenna 230. Hydrogel 110 is preferably only placed where the moisture is expected to reach the sensor while rest of the sensor is made of metal. The first embodiment sensor 100 senses both moisture and pH and provides a larger read range between the sensor 100 and the reader-antenna 230, for example, up to 10 m in range. While silver may be expensive as a material, it is safe for human contact. Moreover, silver ink is printable to facilitate less expensive manufacturing.

Figure 4:
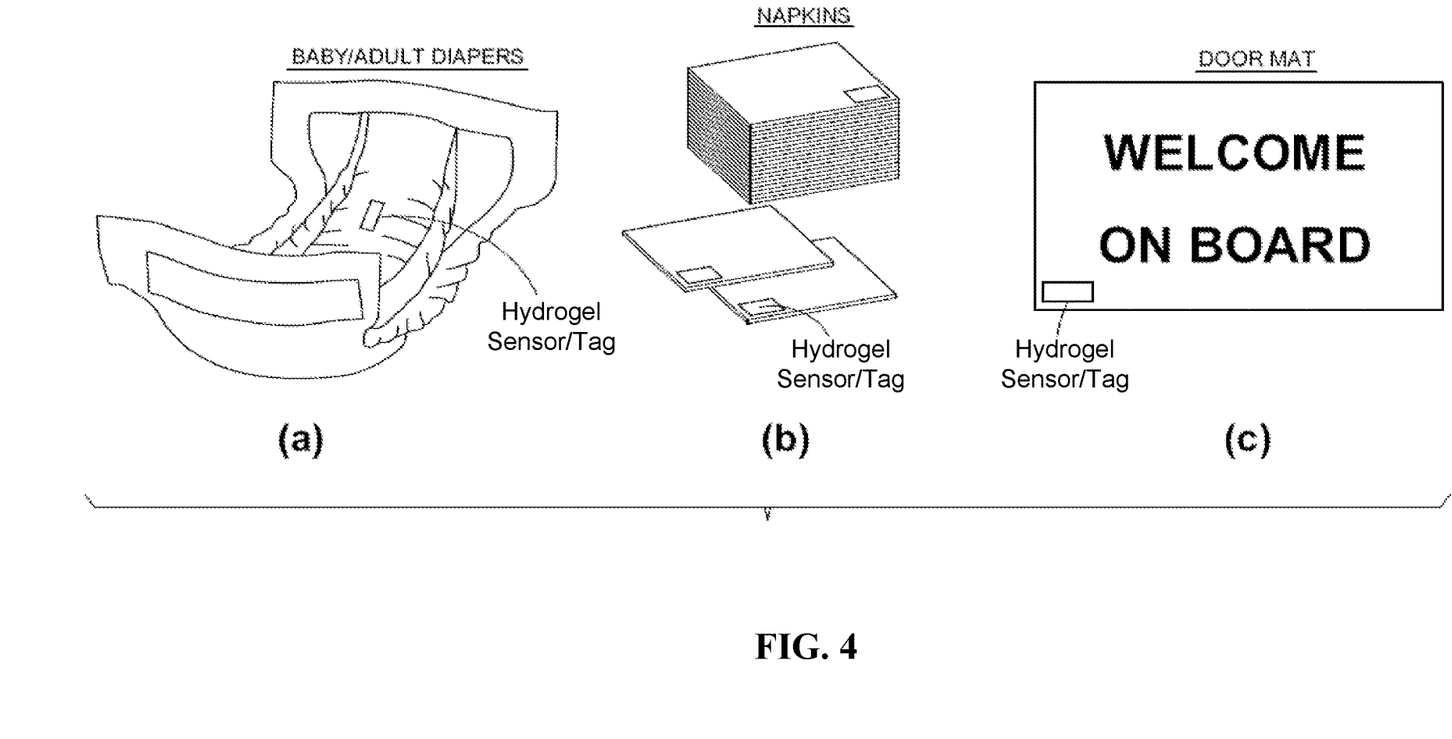
FIG. 4 is a diagram showing applications for the sensor of FIGS. 1A-1B.
Figure 5:
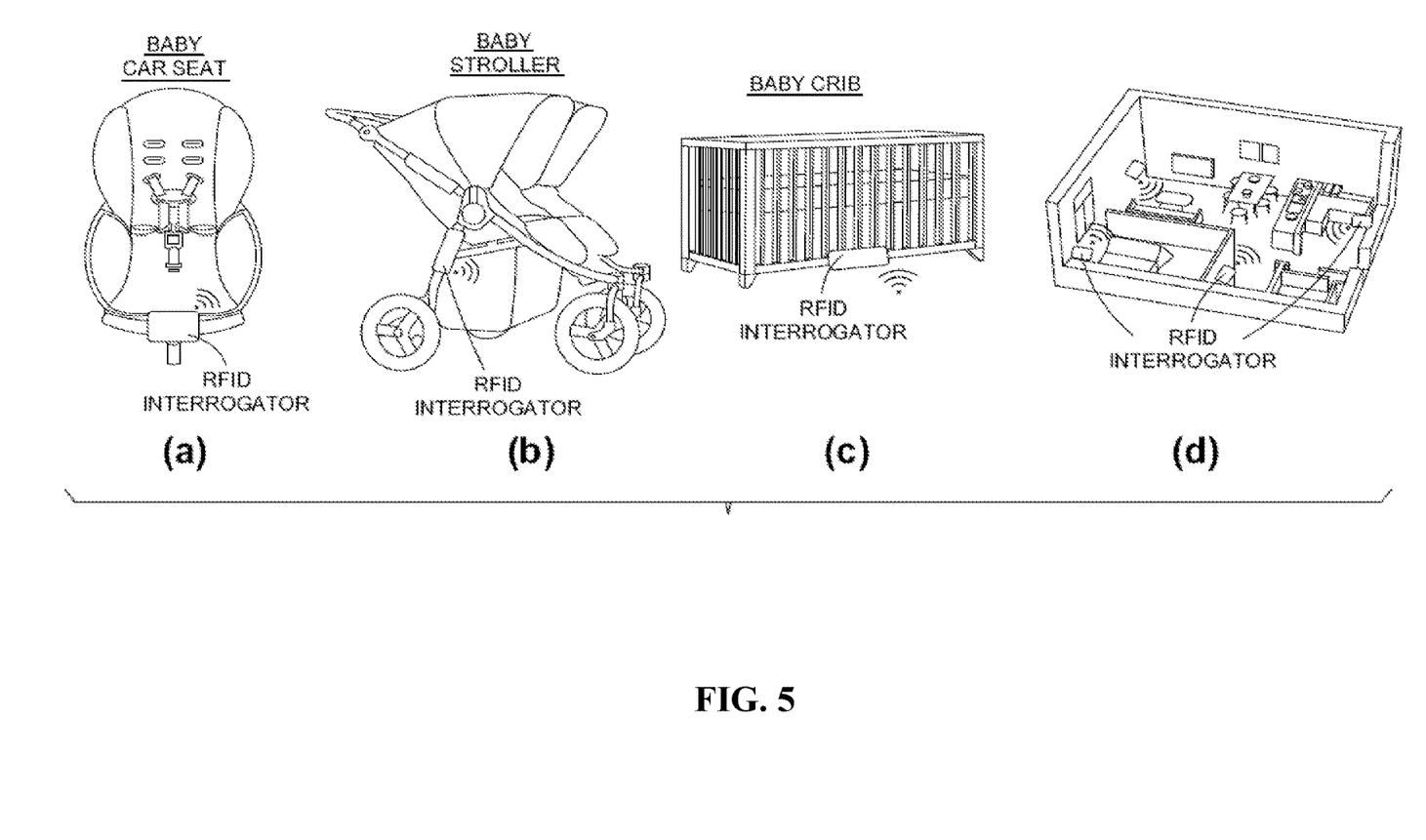
FIG. 5 is a diagram showing applications for the system of FIGS. 2A-2B.

Since the sensors 100, 150 (including the IC 120) are thin, for example, less than 0.5 mm and battery-less, they may easily be embedded into paper/textile-based products such as diapers, napkins, doormats, sheets as illustrated in FIG. 4. Hydrogel material in this work is sensitive to moisture and pH, however, if the hydrogel can be tuned to detect body fluids, glucose, blood, the embedded RFID sensors convert the parent products into smart healthcare monitoring products for everyday use. For example, the chemistry of the hydrogel 110 may be selected to be more responsive to the water molecules or H+ ions present in the low pH fluids. The reader may be, for example, a portable device that can be attached to the baby stroller, crib, car seat or a fixed system mounted onto a wall as shown in FIG. 5.

The RF properties of the sensor 150 change without directly impacting the physical antenna trace. The antenna is made up of conductive hydrogel material. In the event of incident in the diaper, the geometry or shape of the antenna doesn't change significantly. However, the RF properties change significantly because the conductivity of the material changes significantly affecting the impedance matching of the antenna with the IC, radiation pattern, gain, transmission co-efficient, directionality, etc.

Figure 6:
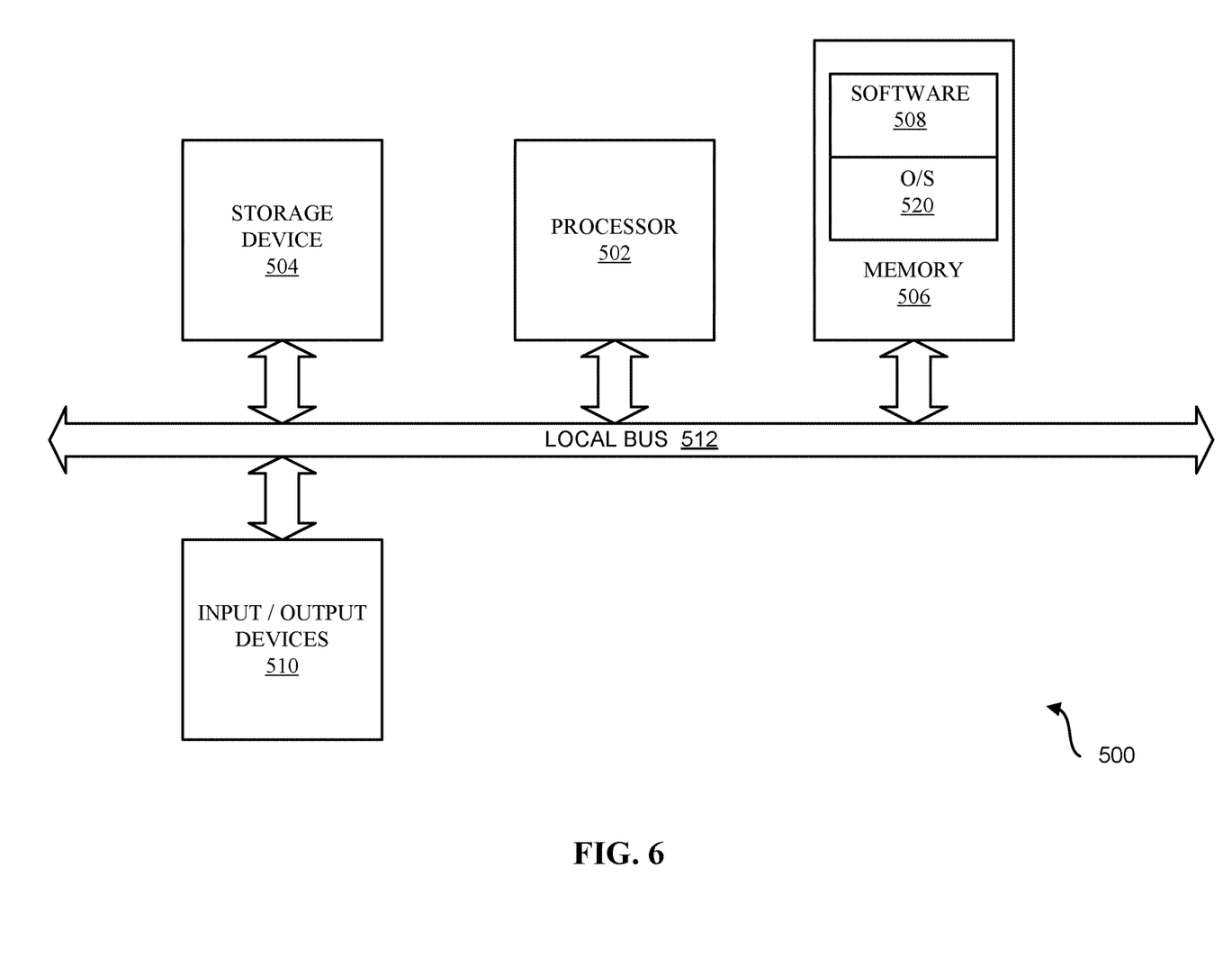
FIG. 6 is a schematic diagram illustrating an example of a system for executing functionality of the present invention.

The present system for executing the functionality described in detail above may include a computer, an example of which is shown in the schematic diagram of FIG. 6. The system 500 contains a processor 502, a storage device 504, a memory 506 having software 508 stored therein that defines the abovementioned functionality, input, and output (I/O) devices 510 (or peripherals), and a local bus, or local interface 512 allowing for communication within the system 500. The local interface 512 can be, for example but not limited to, one or more buses or other wired or wireless connections, as is known in the art. The local interface 512 may have additional elements, which are omitted for simplicity, such as controllers, buffers (caches), drivers, repeaters, and receivers, to enable communications. Further, the local interface 512 may include address, control, and/or data connections to enable appropriate communications among the aforementioned components.

The processor 502 is a hardware device for executing software, particularly that stored in the memory 506. The processor 502 can be any custom made or commercially available single core or multi-core processor, a central processing unit (CPU), an auxiliary processor among several processors associated with the present system 500, a semiconductor based microprocessor (in the form of a microchip or chip set), a macroprocessor, or generally any device for executing software instructions.

The memory 506 can include any one or combination of volatile memory elements (e.g., random access memory (RAM, such as DRAM, SRAM, SDRAM, etc.)) and nonvolatile memory elements (e.g., ROM, hard drive, tape, CDROM, etc.). Moreover, the memory 506 may incorporate electronic, magnetic, optical, and/or other types of storage media. Note that the memory 506 can have a distributed architecture, where various components are situated remotely from one another, but can be accessed by the processor 502.

The software 508 defines functionality performed by the system 500, in accordance with the present invention. The software 508 in the memory 506 may include one or more separate programs, each of which contains an ordered listing of executable instructions for implementing logical functions of the system 500, as described below. The memory 506 may contain an operating system (O/S) 520. The operating system essentially controls the execution of programs within the system 500 and provides scheduling, input-output control, file and data management, memory management, and communication control and related services.

The I/O devices 510 may include input devices, for example but not limited to, a keyboard, mouse, scanner, microphone, etc. Furthermore, the I/O devices 510 may also include output devices, for example but not limited to, a printer, display, etc. Finally, the I/O devices 510 may further include devices that communicate via both inputs and outputs, for instance but not limited to, a modulator/demodulator (modem; for accessing another device, system, or network), a radio frequency (RF) or other transceiver, a telephonic interface, a bridge, a router, or other device.

When the system 500 is in operation, the processor 502 is configured to execute the software 508 stored within the memory 506, to communicate data to and from the memory 506, and to generally control operations of the system 500 pursuant to the software 508, as explained above.

When the functionality of the system 500 is in operation, the processor 502 is configured to execute the software 508 stored within the memory 506, to communicate data to and from the memory 506, and to generally control operations of the system 500 pursuant to the software 508. The operating system 520 is read by the processor 502, perhaps buffered within the processor 502, and then executed.

When the system 500 is implemented in software 508, it should be noted that instructions for implementing the system 500 can be stored on any computer-readable medium for use by or in connection with any computer-related device, system, or method. Such a computer-readable medium may, in some embodiments, correspond to either or both the memory 506 or the storage device 504. In the context of this document, a computer-readable medium is an electronic, magnetic, optical, or other physical device or means that can contain or store a computer program for use by or in connection with a computer-related device, system, or method. Instructions for implementing the system can be embodied in any computer-readable medium for use by or in connection with the processor or other such instruction execution system, apparatus, or device. Although the processor 502 has been mentioned by way of example, such instruction execution system, apparatus, or device may, in some embodiments, be any computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the processor or other such instruction execution system, apparatus, or device.

Such a computer-readable medium can be, for example but not limited to, an electronic, magnetic, optical, electromagnetic, infrared, or semiconductor system, apparatus, device, or propagation medium. More specific examples (a nonexhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted, or otherwise processed in a suitable manner if necessary, and then stored in a computer memory.

In an alternative embodiment, where the system 500 is implemented in hardware, the system 500 can be implemented with any or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

Figure 7:
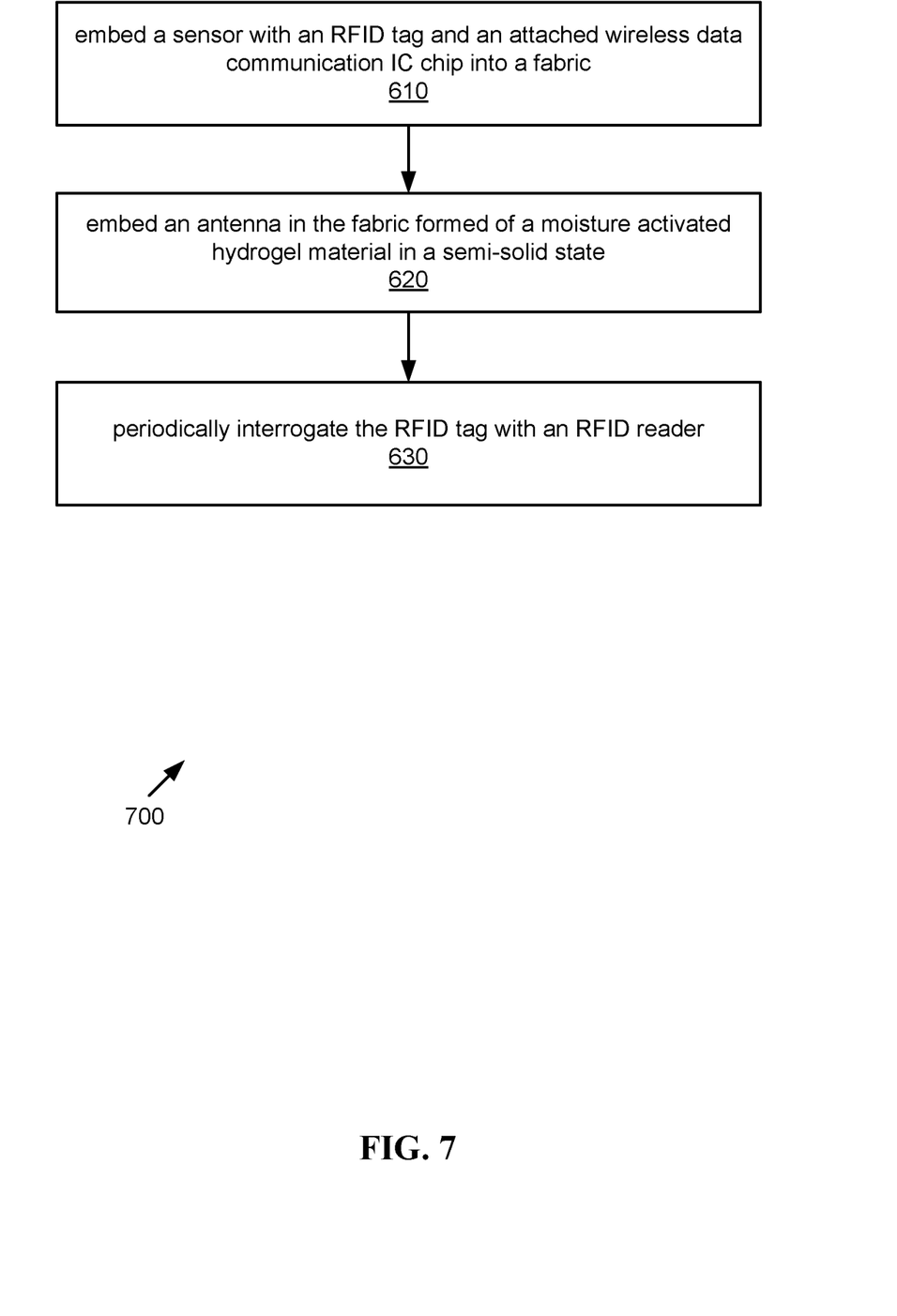
FIG. 7 is a flowchart of an exemplary embodiment of a method for detecting moisture in a fabric.

FIG. 7 is a flowchart of an exemplary embodiment of a method 700 for detecting moisture in a fabric. It should be noted that any process descriptions or blocks in flowcharts should be understood as representing modules, segments, portions of code, or steps that include one or more instructions for implementing specific logical functions in the process, and alternative implementations are included within the scope of the present invention in which functions may be executed out of order from that shown or discussed, including substantially concurrently or in reverse order, depending on the functionality involved, as would be understood by those reasonably skilled in the art of the present invention.

A sensor having a radio frequency identification (RFID) tag and an attached wireless data communication IC chip is embedded in the fabric of, for example, a diaper, as shown by block 610. A moisture activated non-metal antenna is embedded in the fabric, as shown by block 620. The antenna is a moisture responsive hydrogel material in a semi-solid state, and is configured to be inactive prior to an interaction with moisture and active upon the interaction with moisture. The RFID tag is periodically interrogated by an RFID reader, as shown by block 630.

The embodiments described above of a low-cost, pervasively-sensed diaper improve the customer experience of using the product and may be implemented using new business models including data-informed subscriptions. While the embodiments have been directed to a diaper application, the invention may further be applied to other sanitary products, for example, paper towels, sheets, tissues, sanitary napkins etc., wherever moisture or body fluid sensing is applicable. The embodiments may also be applied in other applications, for example food packaging, clothing (for example, to detect sweat), skin patches, glucose detection, and moisture analysis. Hydrogels may also be used in other antenna applications beyond RFID.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An agent activated non-metal antenna for an ultra-high frequency (UHF) wireless sensor having a radio frequency identification (RFID) tag in electronic communication with the non-metal antenna, and a wireless data communication integrated circuit (IC), the non-metal antenna comprising:
    a conductive stimuli-responsive hydrogel material configured to be inactive prior to an interaction with an activating agent and active upon the interaction with the activating agent,
    wherein the non-metal antenna is further configured to transmit power to turn on the wireless data communication IC only when the non-metal antenna is active upon interaction with the activating agent.

2. The antenna of claim 1, wherein the activating agent comprises moisture.

3. The antenna of claim 1, wherein the activating agent comprises an acid and/or base detecting material.

4. The antenna of claim 1, wherein the activating agent comprises a chemical detecting material.

5. The antenna of claim 1, wherein the hydrogel material is configured to expand upon interaction with the activating agent.

6. The antenna of claim 1, wherein the hydrogel material is arranged in a powdery state on a base material.

7. The antenna of claim 6, wherein the base material comprises a fabric.

8. The antenna of claim 6, wherein the hydrogel material is arranged in a shape of an RFID antenna.

9. The antenna of claim 1, further comprising a metal antenna in communication with the non-metal antenna.

10. An ultra-high frequency (UHF) wireless sensor having an agent activated non-metal antenna comprising a conductive stimuli-responsive hydrogel, the sensor comprising:
    a radio frequency identification (RFID) tag in electronic communication with the non-metal antenna; and
    a wireless data communication integrated circuit (IC) in communication with the non-metal antenna and the RFID tag,
    wherein the wireless data communication IC receives power to turn on from the agent activated non-metal antenna.

11. The sensor of claim 10, wherein the RFID tag is a passive RFID tag.

12. The sensor of claim 11, wherein the RFID tag is configured to vary impedance in response to sensing of an activating agent.

13. The sensor of claim 10, wherein the power to turn on the wireless data communication IC derives from a reader that is separate from the sensor, where the non-metal antenna receives electromagnetic energy from the separate reader and uses this energy to drive and transmit the power transmitted to turn on the wireless data communication IC when the non-metal antenna is active.

14. An agent activate antenna for an ultra-high frequency (UHF) wireless sensor having a radio frequency identification (RFID) tag in electronic communication with the antenna, and a wireless data communication integrated circuit (IC), the agent activated antenna comprising:
  a first portion comprising a non-metal stimuli-responsive hydrogel material that becomes conductive in response to an activating agent; and
  a second portion comprising a conductive metal arranged in contact with the first portion; and
  wherein the antenna is configured to be inactive prior to an interaction by the first portion with the activating agent and active upon the interaction by the first portion with the activating agent,
  wherein the non-metal antenna is further configured to transmit power to turn on the wireless data communication IC only when the agent activated antenna is active upon interaction with the activating agent.

15. The antenna of claim 14, wherein the power to turn on the wireless data communication IC derives from a reader that is separate from the sensor, where the antenna receives electromagnetic energy from the separate reader and uses this energy to drive and transmit the power transmitted to turn on the wireless data communication IC when the antenna is active.

\* \* \* \* \*